United States Patent
Franz et al.

(10) Patent No.: US 6,993,964 B2
(45) Date of Patent: Feb. 7, 2006

(54) METHOD OF DETERMINING A MODULUS OF ELASTICITY OF A MOVING WEB MATERIAL

(75) Inventors: Michael J. Franz, Fairfield Township, OH (US); Brian C. Schwamberger, Fairfield Township, OH (US); Matthew D. Dooley, Morrow, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/771,781

(22) Filed: Feb. 4, 2004

(65) Prior Publication Data

US 2005/0166670 A1     Aug. 4, 2005

(51) Int. Cl.
*G01L 5/04*     (2006.01)

(52) U.S. Cl. ................................................ 73/159
(58) Field of Classification Search ............ 73/159, 73/829; 700/122; 428/152; 226/44; 318/6
See application file for complete search history.

(56) References Cited

U.S. PATENT DOCUMENTS

| | | | |
|---|---|---|---|
| 1,851,895 A | 3/1932 | Cornel | |
| 2,634,607 A | 4/1953 | Lawson | |
| 3,366,299 A | 1/1968 | Rose, Jr. et al. | |
| 3,718,037 A | 2/1973 | Stringer et al. | |
| 3,881,346 A * | 5/1975 | Scheucher | 73/829 |
| 3,912,145 A * | 10/1975 | Meihofer | 226/44 |
| 3,933,035 A | 1/1976 | Roch et al. | |
| 4,866,984 A | 9/1989 | Houghton | |
| 5,485,386 A * | 1/1996 | Andreasson | 700/117 |
| 6,517,679 B1 | 2/2003 | Mustonen et al. | |
| 6,752,013 B2 * | 6/2004 | Cote et al. | 73/159 |
| 6,845,282 B2 * | 1/2005 | Franz | 700/122 |
| 6,856,850 B2 * | 2/2005 | Rajala et al. | 700/122 |
| 2003/0078684 A1 | 4/2003 | Martin et al. | |
| 2003/0115946 A1 | 6/2003 | Beuther et al. | |
| 2003/0156344 A1 | 8/2003 | Chliwnyi et al. | |
| 2004/0044432 A1 | 3/2004 | Franz | |
| 2004/0163457 A1 | 8/2004 | Jorkama | |
| 2004/0250628 A1 | 12/2004 | Solberg et al. | |
| 2004/0251370 A1 | 12/2004 | Solberg et al. | |

FOREIGN PATENT DOCUMENTS

EP     0 866 327 A2     9/1998

* cited by examiner

*Primary Examiner*—Max Noori
*Assistant Examiner*—Octavia Davis
(74) *Attorney, Agent, or Firm*—Peter D. Meyer; David K. Mattheis; David M. Weirich (57) ABSTRACT

A method of dynamically determining a modulus of elasticity of a moving web material using web tensions and web velocities. The tension and velocity of a moving web are determined in a first span. The tension and velocity of the moving web are also determined for the moving web in a second span. A value analogous to the modulus of elasticity of the moving web may then be determined according to the tension and velocity values for the moving web in the two spans.

20 Claims, 3 Drawing Sheets

METHOD OF DETERMINING A MODULUS OF ELASTICITY OF A MOVING WEB MATERIAL

FIELD OF THE INVENTION

The invention relates to a method for determining a modulus of elasticity of a moving web. More particularly, the method relates to continuously determining a modulus of elasticity of a moving web.

BACKGROUND OF THE INVENTION

Web materials such as printing, industrial and tissue grades of paper, metal foils, cellulose and polymeric films, wires, ropes, strapping and thread are well known. Products made from these web materials are also well known. Ongoing desires to increase the productivity of the manufacturing operations associated with web materials and web products focus at least in part upon increases in the speed of handling of the web materials. As web handling speeds increase, the adverse effects of web material variations on web handling productivity also increase. Dynamic changes in characteristics such as web tensile strength and web modulus of elasticity, may lead to web breaks when the changes are not adequately compensated for in the web handling process.

The handling of web materials often includes unwinding the material from a roll. The modulus of elasticity of the web material may change over the course of the roll. Changes in the modulus may affect the handling characteristics of the web material. The web material may become more sensitive or less sensitive to changes attempted by the control system of the web handling process. Sensing changes in the modulus of elasticity as the roll is unwound may enable compensatory changes in the web-handling process to offset the changes in the modulus of elasticity while the web is being handled.

The invention provides a method for the dynamic determination of the modulus of elasticity of a moving web material. The determined modulus of elasticity may be used as an input to modify the control scheme of the web-handling process. By sensing changes in the modulus of elasticity, and incorporating the sensed changes into the control scheme, the adverse effects of modulus changes may be mitigated.

SUMMARY OF THE INVENTION

A method for determining the modulus of elasticity of a moving web material is described herein. Web material is transported with an apparatus. The apparatus comprises at least a first span and a second span. A machine-direction web-tension-analog value of the moving web material is determined for each of the first span and second span of the web material. A machine-direction web-velocity-analog value is determined for each of the first span and the second span. A modulus-of-elasticity-analog value for the web may then be determined according to the web-tension-analog values and the web-velocity-analog values for the first span and the second span.

In another aspect of the invention, the web-tension-analog values and web-velocity-analog values are determined and are used to determine a flow-rate-analog value for the web. The flow-rate-analog value and the web-tension and web-velocity-analog values from either the first span or the second span may be used to determine a value for the modulus-of-elasticity-analog value.

BRIEF DESCRIPTION OF THE DRAWINGS

While the claims hereof particularly point out and distinctly claim the subject matter of the present invention, it is believed the invention will be better understood in view of the following detailed description of the invention taken in conjunction with the accompanying drawings in which corresponding features of the several views are identically designated and in which:

DETAILED DESCRIPTION OF THE INVENTION

As used herein:

Modulus-of-elasticity-analog value describes a calculated or determined value analogous to the slope of a stress—strain curve for a material during a deformation of the material.

Web-tension-analog value describes a determined or calculated value analogous to the machine-direction tension of the web material, including values equal to the actual web tension, at a specified point or in a specified span of web material.

Web-velocity-analog value describes a determined or calculated value analogous to a machine-direction velocity of the web material, including values equal to the actual web velocity, at a given point or in a given span of web material.

Flow-rate-analog value, describes a determined or calculated theoretical rate at which an unstrained web would proceed through a portion of a web handling system.

Wound-in-tension-analog value describes a value analogous to the machine-direction forces present in a web in a wound roll of the web material. The value is calculated according to a web's unwinding velocity, the web's modulus-of-elasticity-analog value, and the web's flow-rate-analog value.

Span of web material, process span, or span, describes that portion of a web material in a web handling apparatus lying between a first web contact point and a subsequent web contact point. The web material proceeds through the span from the first web contact point, the upstream end, to the subsequent web contact point, the downstream end.

Unwinding web velocity-analog value, describes a velocity at which a moving web material is unwound from a reel of the web material.

The following description is related in terms of the handling of a single web of material. It will be understood by one of skill in the art that the invention is not limited to systems for handling a single web and that the invention may be used in the handling of multiple webs. As an example, the described invention may be used in the converting of a multiple-ply substrate. In this example, the invention may be used to determine characteristics of one or more of the webs handled by the system. The invention may be used as a portion of the tension and speed control system of one or more webs of a multiple-web-handling system. The invention may be used in a system handling multiple webs that have stress strain properties that are substantially similar. The invention may also be used in a system handling multiple webs wherein the webs have stress strain properties that are moderately or substantially different.

The modulus-of-elasticity-analog value for a moving web material may be dynamically determined according to the tensions and velocities of the moving web material. The modulus-of-elasticity-analog value is considered to be dynamically determined when it is determined for a portion of a web material while that web material portion is moving through a web-handling system. Web-tension-analog values are determined for each of two respective spans of moving web material. Web-velocity-analog values are determined for the same two spans. The two web-tension-analog values and two web-velocity-analog values may then be used to determine a web's modulus-of-elasticity-analog value, and/or flow-rate-analog value.

Figure 1:
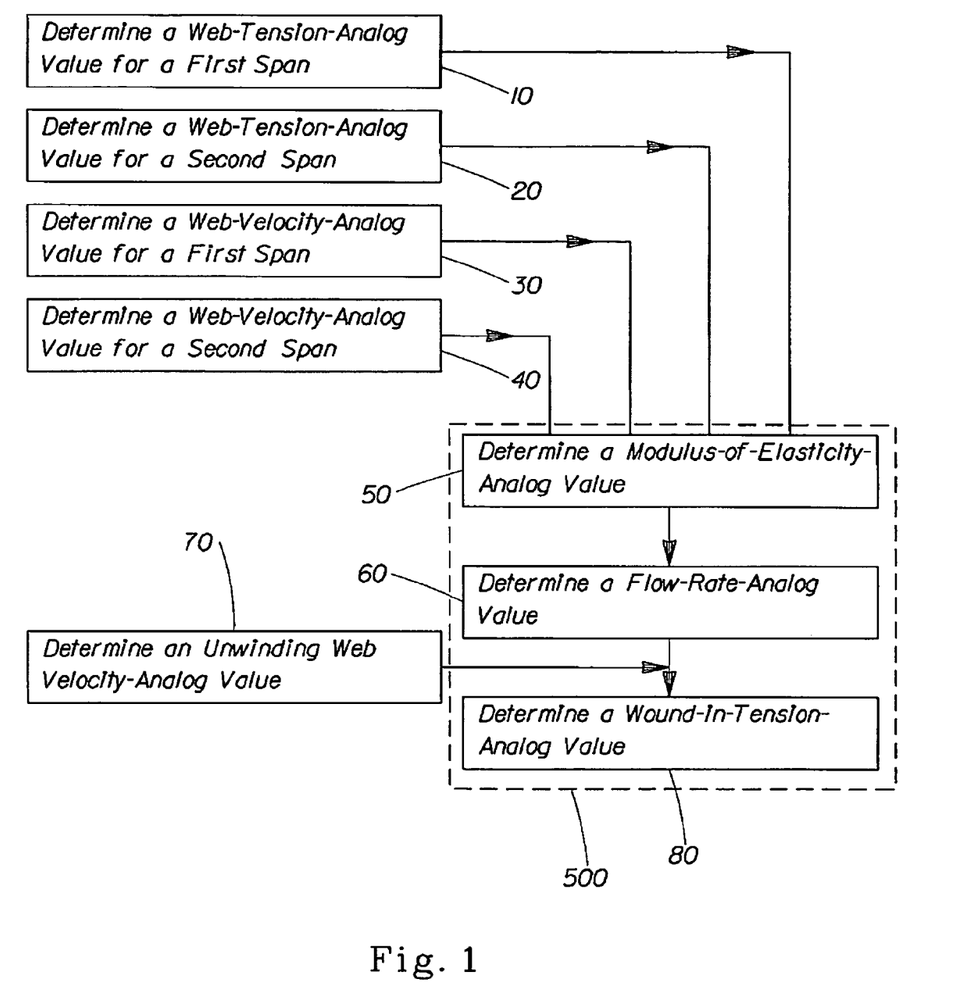
FIG. 1 is a flow chart illustrating the steps of one embodiment of the method of the invention.
Figure 2:
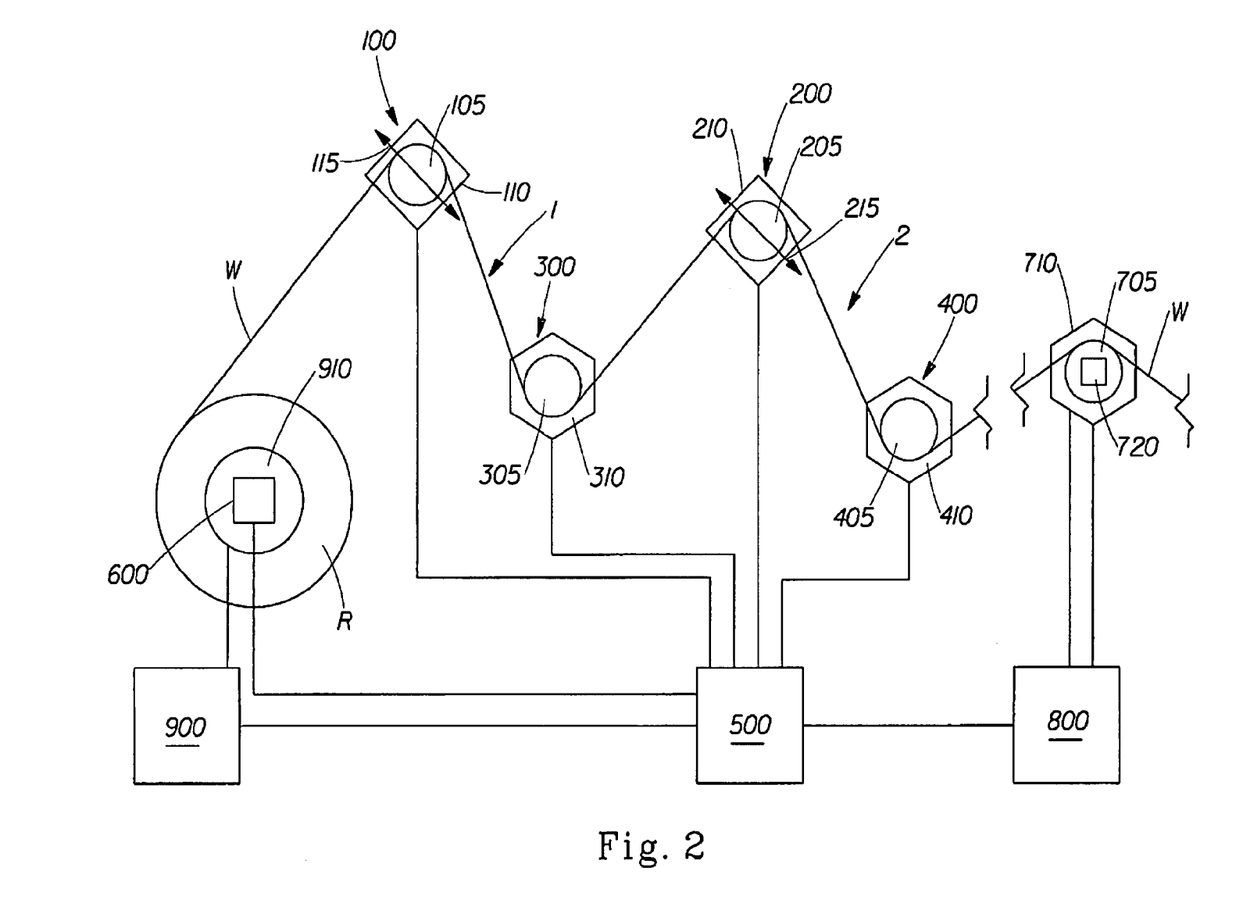
FIG. 2 schematically illustrates a web handling apparatus suitable for the practice of one embodiment of the method of the present invention.

The following steps of one embodiment of the invention are provided as a flow chart in FIG. 1. According to FIG. 1 steps 10 and 20, web-tension-analog values are determined for a first span 1 and a second span 2. According to FIG. 2, the moving web material W, moves sequentially past tension-sensing element 100, velocity-sensing element 300, tension-sensing element 200, and velocity-sensing element 400. According to the figure, elements 100 and 300 define a first span 1, and elements 200 and 400 define a second span 2. The following discussion is in terms of tension-sensing element 100 but is understood to apply as well to tension-sensing element 200 (comprising roller 205 and load cell 210 having sensing axis 215). As shown in FIG. 2, tension-sensing element 100 may comprise an idler roller 105 and a tension-sensing load cell 110. The load cell 110 may have a sensing axis 115 along which force is detected. Tension-sensing element 100, marks the end of an upstream span and the beginning of a downstream span. The sensing axis 115 of the load cell 110 of the tension-sensing element 100 may be oriented perpendicular to the direction of travel of either the upstream span or the downstream span. The load cell 110 will not sense the forces acting perpendicular to the sensing axis 115 of the load cell 110. In this manner, the load cell 110 may be configured to sense only the tension in one span rather than the combined tension in the two spans. This configuration therefore provides a more accurate indication of the tension for a particular span of moving web material W. For the embodiment illustrated in FIG. 2, the load cell 110 is oriented to measure the web-tension-analog value in the span downstream from the tension-sensing element 100. A load cell 110 may be configured such that the load cell senses an analog to the combined tension in the two web segments that share the tension-sensing roller. By orienting the sensing axis 115 such that the axis 115 is not perpendicular to either span, the load cell 110 will sense the analog of the combined tension of the two segments.

In another embodiment, the tension-sensing element may comprise a dancer arm and a spring coupled to a sensor capable of determining the displacement of the spring and of relating that displacement to the web tension. In still another embodiment, the tension-sensing element may be any means known in the art for sensing the tension in a moving web material W including the web-tension sensing means described in commonly assigned, co-pending U.S. patent applications, Ser. Nos. 10/461,321 and 10/461,580, each filed Jun. 13, 2003.

The tension-sensing element senses a force that varies according to the tension in the moving web material W. This force may be equal to, directly proportional to, or otherwise analogous to, the machine-direction tension in the moving web material W. The sensed force analog is considered to be a web-tension-analog value. The terms tension, and tension-analog value as used herein, are each considered to include the actual web tension and any web-tension-analog values.

According to FIG. 1 steps 30 and 40, a first web-velocity-analog value is determined for the first span 1 and a second web-velocity-analog value is determined for the second span 2. The following description is in terms of velocity-sensing element 300 but is understood to apply equally to velocity-sensing element 400 (comprising roller 405 and sensor 410). In one embodiment shown in FIG. 2, velocity-sensing element 300 may comprise a roller 305 and a sensor 310. The roller 305 may be either a powered roller or an idler roller. A mechanical or an electrical encoder, or a resolver, a tachometer, or other means known in the art, may be used to provide a web-velocity-analog value for the moving web material W passing the velocity-sensing element 300. The moving web material W at least partially wraps the roller 305. As the moving web material W passes the roller 305, the roller 305 turns with the web material W without slippage between the roller 305 and the web material W, and the sensor 310 determines the revolutions of the roller 305. The revolutions may be input to a processor 500 that determines the revolutions per unit time. A web-velocity-analog value is determined based upon the known circumference of the roller 305, the pitch diameter of the web, and the revolutions per unit time determined by the processor 500. In another embodiment, the sensor 310 may determine the revolutions of the roller 305 and also determine the revolutions per unit time of the roller 305. In this embodiment, the sensor 310 may provide the revolutions per unit time as an input to a processor 500. In another embodiment, a Doppler laser velocimeter may be used to determine the web-velocity-analog value. Such a velocimeter determines the web-velocity-analog value by sensing the frequency shift in a laser beam caused by the interaction of the beam with the moving web. The velocimeter may provide the determined velocity as an input to a processor 500. In another embodiment, one or both of the velocities may be determined by other web-velocity-sensing means as are known in the art.

Web-velocity-analog values are determined by velocity-sensing elements 300 and 400. The values determined are proportional to, and vary according to, the machine-direction velocity of the moving web material W. The web-velocity-analog values may equal the actual web velocity, or the values may be analogous to the web velocity. The terms velocity, and velocity-analog value as used herein each include the actual web velocity and values analogous to the actual web velocity.

In the embodiment illustrated in FIG. 2, the web material W is unwound from a reel R, and moves through the apparatus. The web-tension-analog values for the first span 1 and the second span 2 are each determined at the upstream end of the respective spans by tension-sensing elements 100 and 200. The web-velocity-analog values for each span are determined at the downstream end of the respective spans by velocity-sensing elements 300 and 400. The four input values are then provided to a processor 500 wherein the modulus-of-elasticity-analog value, and/or flow-rate-analog value for the moving web material W may be determined using the equations described hereinafter.

Figure 3:
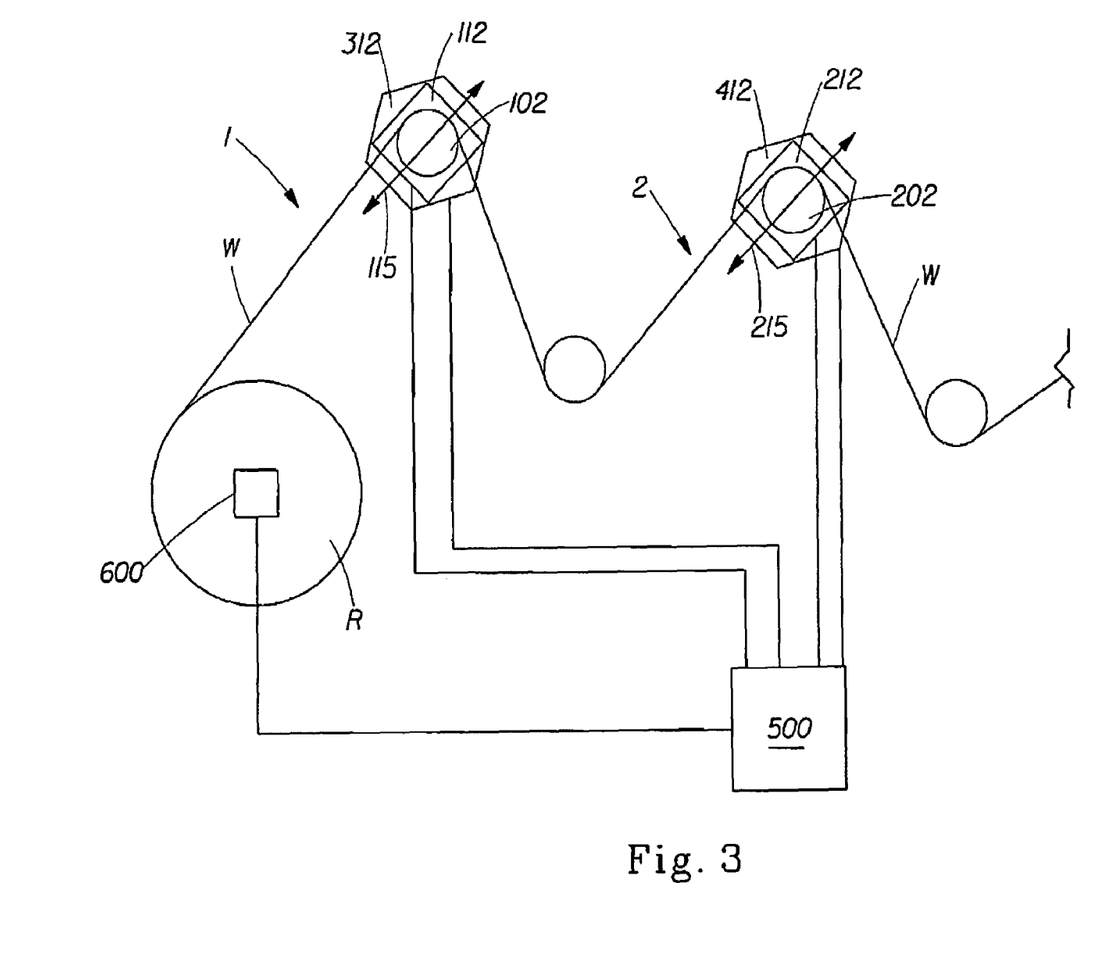
FIG. 3 schematically illustrates a web handling apparatus suitable for the practice of another embodiment of the present invention.

The velocity and tension-analog values of a span may be sensed at a single point for the span. In the embodiment illustrated in FIG. 3, the web-velocity-analog values and the web-tension-analog values for a given span may be determined at a single location by the use of an appropriately instrumented web-handling element. As shown in the figure, the web-tension-analog values and web-velocity-analog values for the first span 1 are determined respectively by sensors 112 and 312, coupled to roller 102. The web-tension-analog values and web-velocity-analog values for the second span are determined respectively by sensors 212 and 412, coupled to roller 202. An idler roller coupled to both an angular-position sensor and to a load cell is a non-limiting example of a web-handling element capable of sensing both web-velocity-analog values and web-tension-analog values. As another example, a laser Doppler velocimeter may be used to determine the web-velocity-analog value at the same point in the web path that the web-tension-analog value is being determined as described above for a particular span of moving web material W.

According to the embodiment illustrated in FIG. 1, steps 50 and 60, the web velocity and tension-analog values are utilized as input values for the method of determining the web modulus-of-elasticity-analog value, and the flow-rate-analog value. The input values are provided to a processor 500 capable of determining the modulus-of-elasticity-analog value $E_w$, step 50, and the flow-rate-analog value $V_O$, step 60, for the moving web material W. The input values may be provided to the processor 500 as either analog signals or digital signals depending upon the output of the particular sensor, the communication link with the processor 500, and the input requirements of the processor 500. In one embodiment, the input sensors may be wired directly to the input circuits of the processor 500. In another embodiment, the input signals may be multiplexed and routed to the processor 500 via a data highway, or information bus, as those terms are known in the art. In yet another embodiment, the input signals may be provided to the processor 500 by way of a wireless connection between each sensor and the processor 500 or between one or more sensor hubs and the processor 500. A sensor hub may receive input signals from at least one sensor and broadcast the signal wirelessly to a receiver that in turn routes the signals to the processor 500. The sensor hub may receive either direct wired, multiplexed, or wireless input signals from the sensors. Any other communication means known in the art may be used to provide the input signals to the processor 500.

The first tension $T_1$, second tension $T_2$, first velocity $V_1$, and second velocity $V_2$, may be conditioned prior to being sent to the processor 500. Exemplary conditioning includes the application of anti-aliasing, smoothing, and limiting filters to the signals. The signals may be conditioned at the input sensor. The sensor hub may filter and/or condition the input signals prior to broadcasting the signals to the processor 500. The input signals may be conditioned after receipt by the processor 500. The input signals may be band pass filtered as is known in the art to remove extraneous noise from the signals and to improve the signal to noise ratio of the signals. The input signals may be low pass filtered, and/or subjected to smoothing filters as are known in the art. The input signals may be time averaged. The time averaging may be a function of the sensor, an intermediate transmission hub, or the averaging may occur at the processor 500. The control system may be configured to constrain the input values between a minimum value and a maximum value to prevent undesirable control loop outputs from resulting. These upper and lower constraints may protect the controlled equipment in the event of a sensor failure or under other conditions when the processor 500 would use aberrant input values.

The processor 500 receives the input signals and determines the modulus-of-elasticity-analog value of the moving web material W. Web tension and web velocity are related to the modulus-of-elasticity-analog value by the equation:

$$T_n = \frac{E_w(V_n - V_0)}{V_0}$$

Where: $T_n$=the web tension in a span n
$E_w$=the modulus-of-elasticity-analog value of the web
$V_n$=the web-velocity-analog value in the span n, and
$V_0$=the flow-rate-analog value of the web.

By determining the tension and velocity of the web for two distinct spans, a system of two equations can be used to solve for $V_0$ and $E_w$. The two equations are:

$$T_1 = \frac{E_w(V_1 - V_0)}{V_0} \text{ and } T_2 = \frac{E_w(V_2 - V_0)}{V_0}$$

Where: $T_1$=the web-tension-analog value in a first span
$T_2$=the web-tension-analog value in a second span
$V_1$=the web-velocity-analog value in the first span, and
$V_2$=the web-velocity-analog value in the second span Solving the two equations for $E_w$ yields the equation:

$$E_w = \frac{(V_2 T_1 - V_1 T_2)}{(V_1 - V_2)}$$

This equation may be used in the processor 500 to determine an $E_w$ that is analogous to the actual modulus of elasticity of the moving web material W.

Alternatively, solving the two equations for $V_O$, yields the equation:

$$V_o = \frac{(V_2 T_1 - V_1 T_2)}{(T_1 - T_2)}$$

This equation may be used in the processor 500 to determine a $V_O$ that is analogous to the actual flow rate of the moving web material W.

The equations may also be used to determine $E_w$ in terms of $V_O$:

$$E_w = \frac{T_1 V_o}{(V_1 - V_o)} \text{ or, } E_w = \frac{T_2 V_o}{(V_2 - V_o)}$$

Or, to determine $V_O$ in terms of $E_w$:

$$V_o = \frac{V_1 E_w}{(E_w + T_1)} \text{ or, } V_o = \frac{V_2 E_w}{(E_w + T_2)}$$

Using the above-developed equations, the processor 500 may be configured to determine $V_O$ based upon the determined value for $E_w$ and input values $T_1$, and $V_1$, or $T_2$, and $V_2$. Alternatively, $V_0$ may be determined using only the input values $T_1$, $V_1$, $T_2$, and $V_2$. In this alternative, $E_w$ may be determined using $V_0$ and the input values $T_1$, and $V_1$, or $T_2$, and $V_2$. In another alternative, the values of $E_w$ and $V_0$ may each be determined using the values of $T_1$, $V_1$, $T_2$, and $V_2$.

According to step 80 of the embodiment illustrated in FIG. 1, the processor 500 may further be configured to determine a wound-in-tension-analog value $T_w$ of the moving web material W. $T_w$ may be determined according to the values of $E_w$, $V_O$, and an unwinding web velocity-analog value $V_u$ of the moving web material W through the equation:

$$T_w = \frac{E_w(V_u - V_o)}{V_o}.$$

$V_u$ may be determined, FIG. 1 step 70, through the means described above for determining a web velocity, or by other means as are known in the art.

The determined $E_w$ may be used in conjunction with a transfer function to adjust the web-handling process relative to a web-converting operation. As an example, embossing a web alters the value of $E_w$ in a predictable manner. This manner may be expressed as a transfer function of $E_w$. This transfer function may be determined according to first principles, empirically, or by other means known in the art. The transfer function may then be used together with the determined $E_w$ to control the web downstream of the embossing operation. The use of the determined $E_w$ and a transfer function downstream of a converting operation may be applied to any converting operation known in the art, and to the converting of single and multiple webs.

$E_w$ and $V_O$ may also be used to determine an on-line value for web strain according to the equations:

$$\text{Strain} = \frac{T}{E_w} = \frac{(V - V_0)}{V_0}$$

Strain may also be considered as the quotient of the change in length and the original length of a stressed web. The determined value for strain may be used as an input in a control system adapted to adjust tension and/or velocity to achieve and maintain a desired value for web strain.

Those portions of the following description relating to the determination of $E_w$, are understood by those of skill in the art to be applicable to the determination of $V_O$, and $T_w$ as well.

Input Value Timing:

In one embodiment of the method, $E_w$ is determined by the processor 500 using concurrently provided values for $T_1$, $T_2$, $V_1$, and $V_2$. $T_1$ and $V_1$ correspond to the passage of a first portion of the moving web material W through a first span. $T_2$ and $V_2$ correspond to the passage of a second portion of the moving web material W through the second span at approximately the same time as the passage of the first web portion through the first span. The processor 500 may determine $E_w$ using the concurrent input values. Concurrent input values are sensed at about the same time. In many cases this concurrent $E_w$ provides an accurate approximation of the $E_w$ of the moving web material W.

In some circumstances, the concurrent $E_w$ determined in the above described manner may not be an accurate enough approximation of the modulus of elasticity of the moving web material W, to be of use. In these circumstances, it may be advantageous to determine $E_w$ using values of $T_1$, $T_2$, $V_1$, and $V_2$, that are associated with the same particular portion of the moving web material W as opposed to values associated with the same time of web handling.

As one example of circumstances under which concurrent determinations of $T_1$, $T_2$, $V_1$, and $V_2$ may yield less than completely satisfactory results, out-of-round rolls induce fluctuations in web tension and velocity as the web material of the rolls is unwound. These fluctuations may be due to the varying diameter of the out-of-round roll and/or the accompanying fluctuation in the distance between the point on the roll circumference where the web unwinds from the circumference (the release point) and the first web-handling component. Over the course of a single revolution of an out-of-round roll, the release point of the web will move toward the first web handling component, and move away from the first web handling component. The oscillating motion of the release point with respect to the first web handling component may cause oscillations in the web's tension and velocity. These oscillations may be unrelated to changes in the modulus of elasticity of the moving web material W. The oscillations may travel or propagate along the web path. $E_w$ is determined according to the web's tensions and velocities. Values of $E_w$ determined according to tension and velocity values that are fluctuating due to the roll being out-of-round may also fluctuate regardless of the actual modulus of elasticity of the moving web material W. It may therefore be advantageous to compensate for this possible source of extraneous tension and velocity fluctuations that can adversely impact the accuracy of a determined $E_w$. It is possible to determine values of $T_1$, $T_2$, $V_1$, and $V_2$ that are associated with the passage of the same portion of moving web material W through each of the first and second spans. Input values determined in this manner are in phase with the fluctuations and may therefore reduce the impact of the fluctuations on the calculations of $E_w$ by the processor 500.

Another example of circumstances under which concurrent determinations of $T_1$, $T_2$, $V_1$, and $V_2$ may yield less than completely satisfactory results is when $E_w$ varies considerably throughout the roll of material being unwound. It is possible that the actual $E_w$ for the web portion in the first span may differ from the actual $E_w$ for the web portion in the second span. For these materials it may be beneficial to determine an $E_w$ that is associated with a single portion of the web material passing through the first span and subsequently passing through the second span. The $E_w$ associated with any particular web portion may then be used to tailor the web handling of that portion of material as the portion proceeds through the web handling system.

The use of time-buffered input values may provide the additional benefits of enabling the determination of more accurate values in less time and decreasing the response time of the control system. These benefits may be provided by a reduction in the need for filtering the input values. The filtering of the input values may be reduced because the input values are in phase and fluctuations between the signals due to phasing may be reduced.

In one embodiment of the method, the values of the tension and the velocity corresponding to the passage of a portion of the web through the first span 1 are stored in a time-buffer for a predetermined amount of time. These time-buffered values are then used by the processor 500, together with the values of tension and velocity corresponding to the passage of the same web portion through the second span to determine an $E_w$ for this portion of the web. The determined $E_w$ corresponds to the modulus of elasticity for the particular web portion. As the modulus of elasticity varies throughout the roll the determined $E_w$ may also vary.

The predetermined time delay for the storage of the time-buffered values from the first span 1 may be determined by considering the known distance between the spans and the determined velocity of the web in each of the spans. With this information it is possible to determine the time a portion of the moving web material W leaving the upstream span takes to reach the corresponding position of the downstream span. The magnitude of the time delay may be dynamically determined by the processor 500 according to the determined velocity of the moving web material W. The web's velocity may vary during the web-handling process, these variations may affect the time elapsed between the handling of the moving web material W by the first span 1 and the handling of the same portion of moving web material W by the second span 2. These changes in velocity may be sensed as described above, or by other means as are known in the art, and provided as an input to the processor 500.

In another embodiment, the magnitude of the time delay may be determined by sensing a mark present on the web W. The first span input values may be determined in association with the sensing of the mark in the first span. The second span input values may be determined in association with the sensing of the mark in the second span. The mark may be an inherent feature of the web W or may be placed upon the web W either during the manufacture of the web or subsequent thereto. The mark may be sensed using any means known in the art appropriate to the particular nature of the mark. Exemplary means include without being limiting, infrared sensors, optical sensors, machine vision systems, magnetic sensors, and proximity sensors.

The processor 500 may be configured to adjust the magnitude of the time delay buffer in accordance with the changes in the web's velocity, or in accordance with the time between the first sensing of a mark and the second sensing of the mark. The magnitude of the time-buffer may be increased as the velocity of the web decreases. The magnitude of the time-buffer may be decreased as the velocity of the web increases. The values of $T_1$ and $V_1$ may thus be held at least until values of $T_2$ and $V_2$ corresponding to the passage of the same portion of moving web material W through the second span 2, are provided as input values to the processor 500. After the values of $T_2$, and $V_2$, corresponding to the handling of the web portion in the second span 2 are provided, $E_w$ may be determined using input values corresponding to the handling of a single portion of moving web material W.

$T_1$, $V_1$, $T_2$, and $V_2$, may be further time-buffered and held until such a time that the processor 500 determines another $E_w$. The time-buffered values may be held and compared to the input signals for $T_1$, $T_2$, $V_1$, and $V_2$ and updated as those input values change. Alternatively, the time-buffered values may be held for a predetermined amount of time and then replaced with either the current input values or a value held in another time-buffer. In this manner, a cascade of time-buffered values corresponding to distinct portions of web material may be held and subsequently used to determine values of $E_w$ associated with corresponding particular portions of moving web material W.

Value Determination Frequency:

In one embodiment, the method of the invention may be used to determine $E_w$ according to a scheduled scan rate of the processor. The scheduled scan rate describes the timing assigned to a given processor task. $E_w$ may be determined during each execution of the processor program. In another embodiment, the processor may be configured to determine $E_w$ each time any of the sensed input values changes. In this embodiment, $E_w$ is only determined when it is likely that a different value for $E_w$ will be determined. As described above, the input values may be held in processor memory until the value of at least one input value changes. When at least one value changes the time-buffered value corresponding to the changed input value may be updated. $E_w$ may then be determined using the time-buffered values.

In another embodiment, the processor 500 may be configured to determine $E_w$ periodically based upon the passage of a predetermined amount of time. As non-limiting examples, the processor 500 may be configured to determine a value for $E_w$ more than once a second, after every one second, ten seconds, thirty seconds, one minute, ten minutes, thirty minutes, or longer time periods of web movement. In still another embodiment, the processor 500 may be configured to determine $E_w$ after the handling of a predetermined amount of web material. As a non-limiting example, the processor 500 may be configured to determine $E_w$ after each 100 feet (30.5 m) of web has been handled.

In another embodiment, the processor 500 may be configured to determine $E_w$ based upon the rotation of the roll R of web material W as the roll R is unwound. As shown in FIG. 2, a sensor 600 may be used to provide an input to the processor 500 that is analogous to the angular position of the roll R of web material W. This sensor 600 may comprise an analog or digital encoder, a resolver, a proximity or optical sensor used in cooperation with a gear, the gear being coupled to the rotation of the roll and the sensor being used to detect a 'zero position' of the gear or to count teeth on the gear and determine the position of rotation accordingly, or both, or other angular position sensors as are known in the art.

The angular position of the roll may then be used to trigger a determination of $E_w$ using either time-buffered or concurrent values of $T_1$, $V_1$, $T_2$, and $V_2$. This embodiment permits the determination of $E_w$ corresponding to angular positions around the circumference of the roll. As an example, this embodiment would permit the determination of a value of $E_w$ corresponding to every ten degrees of rotation of the roll of moving web material W. The ten-degree interval is in no way limiting on the embodiment and the limits on the interval would be linked to the limits of the sensor to resolve the rotational position of the roll, and on the processor 500 to determine a new $E_w$. As a non-limiting example, an encoder capable of resolving a single roll revolution into two million segments may be used as an input to the processor 500 to trigger a calculation of $E_w$, $V_O$, $T_w$, and combinations thereof, two million times per revolution of the roll of moving web material W.

Tension Control:

In one embodiment, the tension of the web material in the initial span, and/or any desired downstream span, may be controlled according to a predetermined tension set-point value. The set-point value may be determined to provide for productive and reliable web handling without exceeding the upper and lower limits of the web material. The upper and lower limits may depend upon the web material characteristics. The limits are related to the tensions at which the web may break or at which unacceptable deformation may occur. The limits may relate to tensions at which the process may yield a finished product of unacceptable quality. In this embodiment, the web-tension-analog value may be determined for the web in the desired span as described above, and the speed of the upstream drive of the span, the downstream drive of the span, or both the upstream and downstream drives, may be varied to maintain the web-tension-analog value at, or around, the predetermined tension set-point value. This variation of the drive speeds may be in addition to the control of the drives to achieve and maintain the desired web processing speeds.

In one embodiment, the unwinding of a roll may be controlled according to the tension in the initial span of the web material. In this embodiment, the unwinding speed of the roll may be varied to maintain a desired web-tension-analog value in the initial span of the web material. During the unwinding of an out-of-round roll, the roll unwinding speed may be varied as the roll unwinds to compensate for the tension fluctuations caused by the fluctuations in the roll diameter. This method of control may reduce the impact of the out-of-round rolls on the tension and velocity of the web in subsequent downstream spans. The unwinding speed of the web may also be varied to compensate for changes in the wound-in-tension of the web material. The changes in the unwinding speed of the web are made according to the output of a controller based upon changes in the sensed tension in the initial span. The controller may perform a control manipulation using a sensed web-tension-analog value, a tension set-point value, the difference between the web-tension-analog value and the tension set-point value (the tension error value) and control loop gain values, to determine the magnitude of the adjustment to the controller output that will reduce the tension error.

The aforementioned controller may be provided as a secondary unit in addition to the previously described processor 500. It is also possible that the processor 500 may provide the functions of determining $E_w$, $V_O$, and $T_w$, as well as providing the functionality of the controller. The following description is in terms of the processor 500 but one of skill in the art will understand that the invention is not limited to the use of a single unit to provide all of the described functions. It will be further understood that the control of the web's tension may be provided by a controller that is distinct from the processor 500. Communications between the processor 500 and a distinct controller may be achieved by any means known in the art.

The method of the invention may be used to determine the modulus of elasticity for any moving web material. The modulus of elasticity may be used as an input for controlling the speed of the web handling equipment according to a desired web tension denoted by a web tension set-point. $E_w$ may be used in the determination of a control loop gain value. The control loop gain value may be used in the control calculation of the processor 500 to determine the adjustment in the processor 500 output necessary to achieve and maintain a desired tension based upon a sensed tension and a desired tension set-point. As the determined $E_w$ changes, the control loop gain value associated with $E_w$ may also change. Dynamic changes to the control loop gain based upon changes in $E_w$ may make the web handling system more responsive to changes in the characteristics of the web material and more reliable.

Without being bound by theory, applicants believe that the modulus of elasticity acts as a process gain in the tension control loop. The rate of response of the web, to changes in the control loop of the web handling process, increases as the modulus of elasticity of the moving web material W increases. The increase in the rate of response may cause the control loop to become undesirably oscillatory and/or unstable. As drive units are adjusted to achieve or maintain a desired web tension set-point, the increased rate of response may cause the control loop to oscillate around the tension set-point. This oscillation may be harmful to the drive system and/or the drive motor. The oscillation may lead to an increased occurrence of web breaks, causing an undesirable loss of productivity. The oscillations may cause undesirable variations in the finished product.

As the modulus of elasticity decreases, the rate of response of the web to control loop changes decreases, resulting in less effective tension control. As the control becomes less effective, the system will be less able to maintain the web at a desired tension set-point. The tension in the web may vary resulting in an inconsistent product and presenting web-handling difficulties due to differences between actual tensions and desired tensions.

Modulus of elasticity compensation (modulus compensation) utilizes the determined $E_w$ value as an input to adjust the gains of the processor 500 control algorithm. These adjustments may produce a more uniform rate of response despite variations in the modulus of elasticity of the web. In a typical Proportional+Integral processor 500 control algorithm, the modulus may be used to determine a value for the proportional gain to achieve a more consistent rate of response for the control loop. As $E_w$ increases, modulus compensation may provide a decreased value for the proportional gain of the system to offset what may otherwise be an increase in the rate of response. As $E_w$ decreases, modulus compensation may provide an increased value for the proportional gain to maintain what may otherwise be a decreased rate of response.

Modulus compensation may be used in conjunction with the method for controlling tension in a web described in commonly assigned co-pending U.S. patent application Ser. No. 10/234,735 filed Sep. 4, 2002. The method of the invention may be used in conjunction with other tension control schemes as are known in the art by serving as an input in the adjustment of process control gains.

In one embodiment illustrated in FIG. 2, modulus compensation may be used to determine an instantaneous value for the control system proportional gain. In this embodiment, the integral gain may be varied according to changes in the tension and/or speed of the web material being handled. A web-tension-analog value may be determined; the web-tension-analog value may be used together with a desired web-tension set-point to determine a web-tension error. Concurrently, a web-velocity-analog value may be determined. The web-velocity-analog value may be used in conjunction with the length of a process span to determine a value for the process instantaneous integral gain to be applied to the process span being controlled. An instantaneous integral gain may be determined according to the ratio of the web-velocity-analog value and the length of the process span, or the reciprocal of this ratio depending upon the configuration of the processor 500 control algorithm. The processor 500 determines an adjusted value for an output based upon the value of the web-tension error using a control calculation. The instantaneous proportional gain and instantaneous integral gains are used in the control calculation to determine the magnitude of the adjustment to the output value. The output value may be communicated from the processor 500 to a drive controller 900. The drive controller 900 may adjust the speed of drive motor 910 to adjust the tension of the web material W.

In another embodiment, a reference integral gain may be determined according to a reference speed value and the length of the process span. The processor instantaneous integral gain may then be varied in proportion to the reference integral gain according to the ratio of the web speed analog value and the reference speed value.

In each of these examples, the web-velocity-analog value may comprise the actual web velocity value as determined by appropriate instrumentation, examples of which are described above, or the web-velocity-analog value may comprise a value proportional to a master speed reference value used to control one or more drive units in the web handling system.

In each of these exemplary embodiments, the control system instantaneous proportional gain value may be varied according to changes in the modulus of elasticity of the web material.

The value of the instantaneous integral gain may be recalculated each time the web's velocity-analog value or tension changes. The value of the instantaneous proportional gain may be recalculated each time $E_w$ changes. Alternatively, the instantaneous integral and proportional gains may be recalculated on a periodic basis using a time-based period or a web-based period. Under a time-based period the value of the instantaneous integral and proportional gains may be recalculated whenever a set period of time elapses. As examples, the value may be recalculated every ten seconds, thirty seconds, or after the passage of any other pre-selected time interval. Under a web-based period, values of the instantaneous integral and proportional gains may be determined each time a pre-selected amount of web material has been handled by the web-handling system.

Particular processor 500 hardware and/or software may limit the lowest web-velocity-analog value for which an instantaneous integral gain may be calculated. The value of the lower limit may be determined according to the specific details of the controlled process. In one embodiment the instantaneous integral gain value may be fixed at any web-velocity-analog value less than 1% of the maximum process speed. In another embodiment the integral gain value may be fixed at any web-velocity-analog value less than 0.1% of the maximum process speed. The speed at which the lower limit of the instantaneous integral gain may be determined is not limited to the above mentioned embodiments. The lower limit speed may be any speed less than the maximum speed of the process. A lower limit instantaneous integral gain may be determined for a selected lower limit web-velocity-analog value. The lower limit instantaneous integral gain may then be used at any web-velocity-analog value less than or equal to the lower limit web-velocity-analog value.

An auxiliary gain, as is known in the art, may be used in conjunction with the above described embodiments to provide an additional parameter for adjusting the control system.

Inferential Web Tension Control:

In a multiple span web handling system utilizing web-tension control, it is common to measure web tension and control web speed to maintain a desired web tension in only a single span. The speeds of all other system spans are then operated as fixed speed spans or have speeds that may be manually adjusted. Determining $E_w$ and $V_0$ as described above, facilitates a method of control wherein the speed of each span may be controlled according to changes in $E_w$ to improve the consistency of the web-handling operation, and to reduce the adverse impact of fluctuations in web modulus of elasticity on productivity.

System speeds, and thereby web tension, may be controlled based upon inferences drawn from changes in $E_w$ and $V_0$ of the moving web material W. For a given span in a web handling process, there is an acceptable operating range for the web tension T and within this range a desired tension $T_D$. $T_D$, $E_w$, and $V_0$, are known. The span velocity $V_n$ necessary to achieve $T_D$, can be determined according to the relationship:

$$V_n = \frac{V_0(E_w + T_D)}{E_w}$$

Handling the moving web material W in a span at a web speed of $V_n$ will result in a web tension of $T_D$, the desired operating tension for the moving web material W.

Returning to FIG. 2, as the moving web material W is unwound, $E_w$ and $V_O$ may be determined and associated with particular portions of the moving web material W. For any $E_w$ and $V_O$ it may be possible to infer what speed $V_n$ would be necessary to maintain the desired tension $T_D$ for a particular web portion. By knowing the lengths of the spans of the web handling system, and by tracking the web velocity as the moving web material W unwinds, it may be possible to determine when any portion of the moving web material W will traverse any particular span for which a desired tension has been determined. Velocity sensor 710 may provide the speed of the web in a particular span measured as the web turns with roller 705. The determined $E_w$, and $V_O$, may be used in the processor 500 to determine a velocity set-point $V_n$ for the span of the web handling apparatus. The velocity set-point may be communicated to a drive controller 800 for the span. Drive controller 800 may apply a speed control loop to drive unit 720 of the span using the velocity input from sensor 710, and the determined velocity set-point from the processor 500. The speed control loop may adjust the speed of the web in the span to the value of $V_n$. This adjustment may achieve and maintain a desired $T_D$ for a web portion, as that portion is handled by each span of the web handling apparatus.

The potential impact of changes in the modulus of elasticity of the moving web material W on web-handling productivity may be reduced by adjusting process span speed controls according to $E_w$ and $V_O$ as web portions associated with changing modulus of elasticity values proceed through the web handling apparatus.

The use of the above described inferential tension control facilitates more consistent web handling without the expense of providing tension sensors and tension control hardware for each span of the web-handling process.

Processor Constraints:

The processor 500 may be constrained to limit the upper values and lower values that may be determined for $E_w$, $T_w$, and $V_O$. The configuration may provide that in the event that the determination of $E_w$, $V_O$, or $T_w$, yields a result above the pre-selected upper limit or below the pre-selected lower limit that the determined value will default to the appropriate limit. As a non-limiting example, a processor 500 may have a pre-selected upper limit for $E_w$ set equal to 6. The processor 500 may determine a value for $E_w$ of 10 according to the inputs. In this instance, the value of $E_w$, used by the processor 500 to determine $V_O$, $T_w$, and/or in the control calculation would default to 6.

The processor may constrain the rate at which the determined values used in subsequent calculations change. As an example, the processor may constrain $E_w$ to change by no more than 50% of the previous value of $E_w$. The percentage of the limit may be any value chosen in accordance with the needs of the process. For processes where a high rate of change is permissible, the percentage may range from 100% to 1000% or greater percentage increases. For processes where the acceptable rate of change is low, the percentage of allowed change may range from 1% to 100%. The value may be chosen based upon empirical data or the experience of the process operator.

The processor 500 may be configured to constrain the output value used in a subsequent control calculation to remain within predetermined absolute limits. As an example, a base proportional gain and a base modulus of elasticity may be determined. The output proportional gain may then be adjusted according to the ratio of the base modulus of elasticity value and the determined modulus-of-elasticity-analog value. This ratio may be constrained to remain within a predetermined range. In one embodiment, the range may be from 0 to 100. In another embodiment the range may be from 0.1 to 50. The range may be determined to provide the desired extent of constraint.

The configuration of the processor 500 may be such that values determined outside pre-selected limits are recorded for subsequent review. The actual value determined as well as the input values leading to that determination may be saved and may further be time stamped or otherwise associated with a registering data value.

Data Storage:

In any of the above-described embodiments, the $E_w$, $V_O$, and $T_w$, that are determined as the roll R of web material is unwound, may be stored as an array. Values of $E_w$, $V_O$, and $T_w$, determined from concurrent input values and/or values determined from time-buffered input values may be stored. The values may be stored with a registration value according to the acquisition frequency of the values. Time based acquisition may configure array data using the time of the value determination as the registration value. Length based determinations may configure array data using sequential lengths as the registration values. Angular position based acquisitions may configure array data using the angular position as the registration values. Other registration values may be determined to provide additional information about the determined values. As an example, the actual location in a roll of the web portion associated with the value of $E_w$ determined according to time-buffered inputs may be determined and stored in the array as well as the acquisition frequency data. Combinations of time registration, length registration, and position registration may also be used.

The compilation of $E_w$, $V_O$, $T_w$, and combinations thereof, into an array enables the compilation of a modulus-of-elasticity profile, a flow-rate profile, a wound-in-tension profile, and combinations of these profiles of the unwound rolls of material. These profiles may be used together with the profiles of similar rolls of web material to determine a typical modulus of elasticity, web flow rate or wound in tension profile for rolls of the particular type involved in the analysis. Any of these profiles may be used to alter the control scheme used to unwind subsequent rolls of the material. The profiles also may be used to predict when changes in the modulus of elasticity may occur within the material of the roll and allow for compensatory changes in the control algorithm.

The profiles may also be used as data to support the use of intelligent or model based control schemes to affect the manufacture and winding of the rolls of web material. As an example, a neural network may take as inputs the operating conditions known during the process of manufacturing and winding a roll of web material that correspond to each portion of the roll of material and associate those known conditions with the modulus of elasticity of the same portion of the roll provided by the roll history. The neural network may then predict changes necessary to the manufacturing and winding conditions to yield a desired profile for modulus of elasticity, web flow rate, wound in tension and combinations thereof in finished rolls. The neural network may then control the manufacturing and winding processes to dynamically implement the predicted changes to produce the desired $E_w$, $V_O$, and $T_w$, profile. The neural network may associate known manufacturing and winding conditions with $E_w$, $V_O$, and $T_w$, values these conditions produced, as provided by the roll modulus of elasticity history. These associations may form the basis for predictions by the neural network of the operating conditions that will yield a desired modulus of elasticity profile in subsequent wound rolls of moving web material W.

$E_w$, $V_O$, and $T_w$, determined at periodic time intervals may be arrayed with the particular interval to which the value corresponds. As an example, a typical array for this embodiment may contain first values of $E_w$, $V_O$, $T_w$, and combinations thereof associated with a first time period, second values of $E_w$, $V_O$, $T_w$, and combinations thereof associated with a second time period and so on.

$E_w$, $V_O$, and $T_w$, determined at periodic web length intervals may be arrayed with the length interval to which the value corresponds. As an example, a typical array for this embodiment may contain first values of $E_w$, $V_O$, $T_w$, and combinations thereof, associated with a first web length, second values of $E_w$, $V_O$, $T_w$, and combinations thereof, associated with a second web length, and so on.

$E_w$, $V_O$, and $T_w$, determined at periodic rotational position intervals may be arrayed with the rotational position interval to which the value corresponds. As an example, a typical array for this embodiment may contain first values of $E_w$, $V_O$, $T_w$, and combinations thereof, associated with a first rotational position, second values of $E_w$, $V_O$, $T_w$, and combinations thereof, associated with a second rotational position, and so on.

In an embodiment wherein $E_w$, $V_O$, $T_w$, and combinations thereof are determined whenever any of the input values change, the array may comprise data points of $E_w$, $V_O$, $T_w$, and combinations thereof, together with the length of web material processed since the last determination of $E_w$, $V_O$, $T_w$, and combinations thereof.

These arrays may provide profiles of modulus of elasticity, flow rate, wound in tension and combinations thereof for a given roll. These profiles may illustrate changes in $E_w$, $V_O$, $T_w$, and combinations thereof, in the web material from the beginning to the end of the roll. The arrays may allow a reconstruction of the profiles of roll modulus of elasticity, flow rate, wound in tension, and combinations thereof, based upon the position within the roll of the web segment corresponding to particular $E_w$, $V_O$, $T_w$, and combinations thereof. In any of the above embodiments, a roll position may be determined and associated with the respective web portions. This roll location may be stored as part of the array in association with the values determined for the respective web portions.

In one embodiment, the processor 500 may create and store the above described data array within the memory of the processor 500. In another embodiment, the processor 500 may export the values comprising the array to a secondary processor, or other means, configured to construct and/or store the array. In yet another embodiment, the processor 500 may export the values to one or more secondary processors. In this embodiment, the secondary processor or processors may compile the array data points and store the array or pass the compiled data points to yet another processor or data storage device.

Modulus-of-Elasticity-Analog Value Source:

The modulus-of-elasticity-analog value used as described above may be provided as described above, by the use of known on-line ultrasonic sensors, or by any means known in the art.

EXAMPLE 1

Paper web is unwound from a large parent roll for converting the web into a consumer paper product. The web is wrapped around a first idler roller. The idler roller is coupled to a pair of ABB Pressductor load cells model number PFTL301E. The Pressductor load cells receive control power from, and provide output signals to, an ABB Tension Electronics unit PFEA111. The Tension Electronics unit low-pass filters the input signals. The load cells and tension electronics unit are available from ABB, Brewster, N.Y. The Tension Electronics unit amplifies the signal from the load cells yielding a 0–10 Volt analog output signal. The output of the Tension Electronics unit is hard wired to an input circuit board of a Robox RBXM Modular Motion controller available from Robox S.P.A., Ticino, Italy.

Velocity inputs are derived from encoders coupled to drive motors and also to powered rollers. The drive motors and powered rollers are components of the web handling system. A Siemens drive motor comprising an integral encoder, available from Siemens AG of New York, N.Y., and a TR Electronics incremental encoder model IE58a available from TR Electronic Inc. of Troy, Mich. are exemplary, non-limiting encoders. The encoders provide respective outputs of 4096 and 3000 pulses per revolution, and are hardwired to the controller encoder input circuits. The controller receives the output pulses of the encoders as input pulses and converts the input pulses to revolutions per second, and then to a velocity, using the known circumference of the web contacting roller, and the processor clock.

The velocity and tension input signals are first-order filtered and time buffered by the Robox controller and subsequently used to determine values for $E_w$. A predetermined base modulus of elasticity value set in the Robox controller is divided by the determined $E_w$ value to determine a modulus ratio. The modulus ratio is then multiplied by a base proportional gain set in the Robox controller to determine an instantaneous proportional gain. As the determined $E_w$ increases, the modulus ratio decreases and the instantaneous proportional gain value decreases. The modulus ratio is constrained between 0.5 and 1.5.

The instantaneous proportional gain is used in the Robox controller control calculation to determine the controller output. The Robox controller output is a 0–10 volt analog signal provided to an Allen-Bradley 1336 Force Drive, available from Allen-Bradley, Milwaukee, Wis. The model 1336 Force Drive unit subsequently adjusts the speed of a controlled motor in the web-handling process. As the modulus of elasticity of the web changes, the determined value of $E_w$ changes. The proportional gain changes according to changes in $E_w$, and the output to the drive controller changes according to the proportional gain. The speed of the controlled motor changes according to the changes in the output to the drive controller.

The determined $E_w$ value and either $T_1$, and $V_1$, or $T_2$, and $V_2$, are used to determine a value for $V_O$. The determined values for $E_w$, and $V_O$, are subsequently used to calculate a web speed set-point based upon a desired tension, for each span. The velocity-analog value for a particular span may be provided by an encoder coupled to a roller or motor in that span. A speed control loop for each particular span may then be applied to the span using the calculated speed set-point and the velocity-analog value for the span. As the determined $E_1$ and $V_O$ change, the speed set-point value may change and the speed of the motor controlled by the speed control loop may change.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would have been obvious to those skilled in the art that various other changes and modifications can be made without departing from the spirit and scope of the invention. It is therefore intended to cover in the appended claims all such changes and modifications that are within the scope of the invention.

What is claimed is:

1. A method of determining a modulus-of-elasticity-analog value of a moving web material, the method comprising steps of:
    a) determining a first web-tension-analog value of the moving web material in a first span,
    b) determining a first web-velocity-analog value of the moving web material in the first span,
    c) determining a second web-tension-analog value of the moving web material in a second span,
    d) determining a second web-velocity-analog value of the moving web material in the second span, and
    e) determining the modulus-of-elasticity-analog value of the moving web material according to the first web-tension-analog value, the second web-tension-analog value, the first web-velocity-analog value, and the second web-velocity-analog value.

2. The method according to claim 1 wherein the first web-tension-analog value and the first web-velocity-analog value are determined at a first location.

3. The method according to claim 1 further comprising a step of determining a flow-rate-analog value of the moving web material according to the modulus-of-elasticity-analog value and either the first web-tension-analog value and the first web-velocity-analog value, or the second web-tension-analog value and the second web-velocity-analog value.

4. The method according to claim 3 further comprising steps of:
    a) determining an unwinding web velocity-analog value of the moving web material, and
    b) determining a wound-in-tension-analog value of the moving web material according to the flow-rate-analog value, the modulus-of-elasticity-analog value and the unwinding web velocity-analog value.

5. The method according to claim 3 comprising a step of determining a flow-rate-analog value whenever there is a change in any value selected from either the group consisting of: the first web-tension-analog value, the first web-velocity-analog value and combinations thereof, or the group consisting of: the second web-tension-analog value, the second web-velocity-analog value, and combinations thereof.

6. The method according to claim 1 wherein the first web-tension-analog value is determined for a first web portion in a first span, and the second web-tension-analog value is determined for the first web portion in a second span.

7. The method according to claim 1 further comprising a step of determining a modulus-of-elasticity-analog value whenever there is a change in any value selected from the group consisting of: the first web-tension-analog value, the first web-velocity-analog value, the second web-tension-analog value, the second web-velocity-analog value, and combinations thereof.

8. The method according to claim 1 wherein the modulus-of-elasticity-analog value is determined at predetermined time intervals.

9. The method according to claim 1 wherein the modulus-of-elasticity-analog value is determined after the handling of a predetermined length of moving web material.

10. The method according to claim 1 wherein the modulus-of-elasticity-analog value is determined according to a rotational position of the roll.

11. The method according to claim 1 comprising steps of:
 a) unwinding the moving web material from a roll of web material,
 b) associating at least a first web portion with a roll coordinate location,
 c) determining a modulus-of-elasticity-analog value for at least the first web portion, and
 d) associating the modulus-of-elasticity-analog value determined for the first web portion with the roll coordinate location associated with the first web portion.

12. The method according to claim 11 further comprising steps of:
 a) associating a time value with the determined modulus-of-elasticity-analog value, and
 b) storing at least the modulus-of-elasticity-analog value with the associated time value.

13. The method according to claim 11 further comprising steps of:
 a) determining a flow-rate-analog value for the first web portion, and
 b) associating the flow-rate-analog value for the first web portion with the roll coordinate location of the first web portion.

14. The method according to claim 13 further comprising steps of:
 a) determining an unwinding web velocity-analog value for the first web portion,
 b) determining a wound-in-tension-analog value for the first web portion, and
 c) associating the unwinding web velocity-analog value and the wound-in-tension-analog value with the roll coordinate location of the first web portion.

15. The method according to claim 14 further comprising a step of storing a data value with an associated registration value, the data value selected from the group consisting of: the modulus-of-elasticity-analog value, the flow-rate-analog value, the wound-in-tension-analog value, and combinations thereof.

16. The method according to claim 14 comprising at least partially filtering at least one value selected from the group consisting of: the first web-tension-analog value, the second web-tension-analog value, the first web-velocity-analog value, the second web-velocity-analog value, the modulus-of-elasticity-analog value, the flow-rate-analog value, and combinations thereof.

17. The method according to claim 16 including high frequency filtering of at least the first web-tension-analog value measurement.

18. A method of determining a modulus-of-elasticity-analog value of a moving web material, the method comprising steps of:
 a) determining a first web-tension-analog value of the moving web material in a first span,
 b) determining a first web-velocity-analog value of the moving web material in the first span,
 c) determining a second web-tension-analog value of the moving web material in a second span,
 d) determining a second web-velocity-analog value of the moving web material in the second span,
 e) determining a flow-rate-analog value of the moving web material according to the first web-tension-analog value, the second web-tension-analog value, the first web-velocity-analog value, and the second web-velocity-analog value, and
 f) determining the modulus-of-elasticity-analog value according to the flow-rate-analog value and either the first web-tension-analog value and the first web-velocity-analog value, or the second web-tension-analog value and the second web-velocity-analog value.

19. The method according to claim 18 further comprising steps of:
 a) determining an unwinding web velocity-analog value for the moving web material, and
 b) determining a wound-in-tension-analog value for the moving web material according to the modulus-of-elasticity-analog value, the flow-rate-analog value and the unwinding web velocity-analog value.

20. A method of determining a modulus-of-elasticity-analog value of a moving web material, the method comprising steps of:
 a) determining a first web-tension-analog value of a first portion of the moving web material in a first span,
 b) determining a first web-velocity-analog value of the first portion of the moving web material in the first span,
 c) determining a second web-tension-analog value of the first portion of the moving web material in a second span,
 d) determining a second web-velocity-analog value of the first portion of the moving web material in the second span,
 e) determining the modulus-of-elasticity-analog value of the moving web material according to at least the first web-tension-analog value, the second web-tension-analog value, the first web-velocity-analog value, and the second web-velocity-analog value, and
 f) determining a flow-rate-analog value according to at least the first web-tension-analog value, the second web-tension-analog value, the first web-velocity-analog value, and the second web-velocity-analog value.

* * * * *

UNITED STATES PATENT AND TRADEMARK OFFICE
CERTIFICATE OF CORRECTION

PATENT NO. : 6,993,964 B2
APPLICATION NO. : 10/771781
DATED : February 4, 2004
INVENTOR(S) : Franz et al.

It is certified that error appears in the above-identified patent and that said Letters Patent is hereby corrected as shown below:

Col. 16, line 9, the word "roil" should be deleted and the word --roll-- should be inserted therefor.

Signed and Sealed this

Seventh Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,993,964 B2 | Page 1 of 1 |
| APPLICATION NO. | : 10/771781 | |
| DATED | : February 7, 2006 | |
| INVENTOR(S) | : Franz et al. | |

It is certified that error appears in the above-identified patent and that said Letters Patent is hereby corrected as shown below:

Col. 16, line 9, the word "roil" should be deleted and the word --roll-- should be inserted therefor.

This certificate supersedes Certificate of Correction issued November 7, 2006.

Signed and Sealed this

Twelfth Day of December, 2006

JON W. DUDAS
*Director of the United States Patent and Trademark Office*